United States Patent [19]

Kondo et al.

[11] 4,188,492

[45] Feb. 12, 1980

[54] PROCESS FOR CONVERTING 2,2-DICHLOROVINYLCYCLOPROPANES TO DIBROMOVINYL ANALOGS

[75] Inventors: Kiyoshi Kondo; Kiyohide Matsui, both of Kanagawa, Japan

[73] Assignee: FMC Corporation, Philadelphia, Pa.

[21] Appl. No.: 737

[22] Filed: Jan. 3, 1979

Related U.S. Application Data

[63] Continuation-in-part of Ser. No. 875,650, Feb. 6, 1978, abandoned.

[51] Int. Cl.$^2$ .................... C07C 51/00; C07C 67/30
[52] U.S. Cl. .................................. 562/506; 560/124
[58] Field of Search ....................... 560/124; 562/506

[56] References Cited

U.S. PATENT DOCUMENTS 2,553,518  5/1951  Lake .................................. 260/544

OTHER PUBLICATIONS

Bailar, "Comprehensive Inorganic Chemistry," p. 1013 (Pregamon Press, Oxford, Eng., 1973).
Gattermann–Wieland, "Laboratory Methods of Organic Chemistry," pp. 342–343 (Macmillan & Co., London, England, 1952).
Jolles, "Bromine and Its Compounds," pp. 383–384 (Academic Press, New York, N.Y. 1966).
Mellor, "Inorganic and Theoretical Chemistry," vol. V, pp. 324–327 (Longmans, Green & Co., New York, N.Y., 1956).
Trotter, J. Org. Chem. 28, p. 2093 (1963).
Yagupolskii, J. Gen. Chem., USSR, 37, p. 1686, (1967).

*Primary Examiner*—Howard T. Mars
*Assistant Examiner*—Michael Shippen
*Attorney, Agent, or Firm*—Richard L. Hansen; Henry R. Ertelt

[57] ABSTRACT

Treatment of 3-(2,2-dichlorovinyl)-2,2-dimethylcyclopropanecarboxylic acids and esters with aluminum bromide, the reaction product of aluminum and a bromoalkane, or HBr and the product of the reaction of HBr with aluminum or an aluminum salt produces the 3-(2,2-dibromovinyl)-2,2-dimethylcyclopropane analogs.

6 Claims, No Drawings

PROCESS FOR CONVERTING 2,2-DICHLOROVINYLCYCLOPROPANES TO DIBROMOVINYL ANALOGS

This application is a continuation in part of application Ser. No. 875,650, filed Feb. 6, 1978, now abandoned.

This invention relates to a process for converting 2,2-dichlorovinylcyclopropanecarboxylic acids and esters into the corresponding dibromovinyl compounds.

The prior art describes chemical products and processes for preparing 3-(2,2-dihalovinyl)-2,2-dimethylcyclopropanecarboxylic acids. Such carboxylic acids are of interest because they may be readily esterified with certain alcohols to produce potent new pyrethroid insecticides, such as those described in U.S. Pat. No. 4,024,163. Among the new pyrethroid insecticides, some of the most potent contain the cis-3-(2,2-dibromovinyl)-2,2-dimethylcyclopropanecarboxylic acid unit.

Thus, the object of the instant invention is to provide a process for producing 3-(2,2-dibromovinyl)-2,2-dimethlcyclopropanecarboxylic acid, especially cis-3-(2,2-dibromovinyl)-2,2-dimethylcyclopropanecarboxylic acid, or its lower alkyl esters, from the corresponding dichlorovinyl analogs. Either the dibromovinyl acid or lower alkyl esters thereof may be transformed into insecticidal 3-(2,2-dibromovinyl)-2,2-dimethylcyclopropanecarboxylates by methods well known in the art, as disclosed in U.S. Pat. No. 4,024,163, for example, which disclosure is incorporated herein by reference.

According to this invention there is provided a process for preparing 3-(2,2-dibromovinyl)-2,2-dimethylcyclopropanecarboxylic acid or a lower alkyl ester thereof which comprises exchanging the chlorine atoms in 3-(2,2-dichlorovinyl)-2,2-dimethylcyclopropanecarboxylic acid or a lower alkyl ester thereof with bromine atoms.

For purposes of this invention, a lower alkyl ester is an ester wherein the alcohol moiety contains 1–6, preferably 1–4, carbon atoms.

One of the unexpected advantages of this invention is that the halogen exchange proceeds without affecting the stereochemical configuration of the dichlorovinyl starting material; another feature is the surprisingly high yield obtained. Thus, for example, halogen exchange of ethyl cis-3-(2,2-dichlorovinyl)-2,2-dimethylcyclopropanecarboxylate according to the process of this invention produces ethyl cis-3-(2,2-dibromovinyl)-2,2-dimethylcyclopropanecarboxylate, and cis-3-(2,2-dichlorovinyl)-2,2-dimethylcyclopropanecarboxylic acid produces cis-3-(2,2-dibromovinyl)-2,2-dimethylcyclopropanecarboxylic acid [see U.S. Pat. No. 4,024,163 for an explanation of nomenclature]. Yields exceeding 90% have been obtained.

In the process of this invention 3-(2,2-dichlorovinyl)-2,2-dimethylcyclopropanecarboxylic acid, or a lower alkyl ester thereof, such as ethyl 3-(2,2-dichlorovinyl)-2,2-dimethylcyclopropanecarboxylate or methyl 3-(2,2-dichlorovinyl)-2,2-dimethylcyclopropanecarboxylate, is treated with aluminum bromide, the reaction product of aluminum and a bromoalkane containing 1–6, preferably 1–4, carbon atoms, or HBr and the product of the reaction of HBr with aluminum or an aluminum salt.

Although aluminum bromide may be employed as such, it can be prepared in situ by the reaction between aluminum and bromine. Alternately, the reaction product obtained by dissolving aluminum in a bromoalkane can be used. In using either aluminum bromide or the reaction product of aluminum and a bromoalkane, between one and two moles of aluminum, either as aluminum bromide or the aforesaid reaction product, preferably about 1.5 moles, per mole of dichlorovinyl compound are employed. The halogen exchange is advantageously conducted in a solvent, preferably, a solvent in which aluminum bromide is at least partially soluble, e.g., methylene bromide, ethylene bromide, ethyl bromide, carbon disulfide, methylene chloride, and cyclohexane. Among these solvents, methylene bromide is preferred when aluminum bromide is employed as such or prepared in situ, and ethylene bromide is preferred when aluminum is dissolved in a bromoalkane. Although the exchange reaction will occur at elevated temperatures, e.g., as high as the normal boiling points of the solvents, it also occurs below room temperature, e.g., between about 0° and 10° C., and even at lower temperatures. Although not required, an acid scavenger, for example, aluminum or a base, such as sodium carbonate, may be present in the reaction mixture during or in the final stages of the reaction, and use of such a scavenger is preferred. Aluminum is preferred for this purpose.

When the exchange is conducted with HBr and the product of the reaction of HBr with aluminum or an aluminum salt, it is necessary that at least one mole of aluminum or aluminum salt be employed per mole of dichlorovinyl compound, and the best yields result when the ratio is about 1.5/1, the aluminum or aluminum salt being in excess. Aluminum foil, ribbon or shot is readily available and preferred, and a number of aluminum salts are satisfactory, viz., aluminum chloride or aluminum bromide, but between the latter aluminum chloride is less expensive and so the preferred salt. The reaction is advantageously carried out in a solvent; for example, a solvent selected from those listed above, but a brominated solvent, especially methylene bromide is preferred, at temperatures ranging from about 0° C. to the boiling point of the solvent. Although not required, the reaction is preferably conducted under an inert atmosphere such as argon or nitrogen, and it is especially preferred to sparge the reaction mixture with an inert gas just before isolating the product.

The process of this invention will be understood more readily by reference to the following examples which illustrate it. In the examples which follow temperatures are in degrees Celsius and pressures are in mm Hg.

EXAMPLE I

Preparation of Ethyl 3-(2,2-Dibromovinyl)-2,2-Dimethylcyclopropanecarboxylate using Aluminum Bromide To a solution of ethyl 3-(2,2-dichlorovinyl)-2,2-dimethylcyclopropanecarboxylate (14.81 g, 0.0625 mole) in 30 ml of ethylene bromide was added dropwise at 0° a solution of aluminum bromide (25 g, 0.094 mole) in 20 ml of ethylene bromide. After stirring for 4½ hours, the solution was poured into a mixture of ice and water. The resultant mixture was extracted three times with ether. The ether extracts were combined and successively washed twice with water, twice with aqueous sodium bicarbonate, twice with aqueous sodium chloride, and then dried over anhydrous magnesium sulfate. The ether was then removed by evaporation, leaving a residue. The residue was dissolved in n-hexane, and 1,5-diazabicyclo[5.4.0] undec-5-ene was added to the solution. Dimethylformamide was added as a cosolvent. The solution was poured into dilute aqueous hydrochloric acid at 0°. The resultant mixture was extracted with ether. The ether extract was washed with water, aqueous sodium bicarbonate, aqueous sodium chloride, and then dried. The ether was removed, and the residue was distilled under reduced pressure to afford ethyl 3-(2,2-dibromovinyl)-2,2-dimethylcyclopropanecarboxylate (16.28 g, 87% yield); bp, 104–106°/0.28 mm.

EXAMPLE II

Preparation of Ethyl 3-(2,2-Dibromovinyl)-2,2-Dimethylcyclopropanecarboxylate Using Aluminum Bromide Prepared In Situ Bromine (2.56 g, 0.016 mole) was added to a small portion of aluminum foil (total 0.432 g, 0.016 mole) suspended in 8 ml of methylene bromide. The suspension was heated with a flame until an exothermic reaction began. The remaining aluminum foil was then added slowly, a little at a time. After the aluminum had all dissolved, the mixture was allowed to cool to room temperature, and the resulting black mixture was transferred dropwise to a solution of ethyl 3-(2,2-dichlorovinyl)-2,2-dimethylcyclopropanecarboxylate (2.37 g, 0.010 mole) in 7 ml methylene bromide at 0°. When the addition was complete, the reaction mixture was stirred overnight at room temperature.

The reaction mixture was then divided into three portions, to which were added aluminum foil, pyridine, and sodium carbonate, respectively. After periods of time ranging from 1 to 5 hours, the three mixtures were examined by vapor phase chromatography; each mixture contained ethyl 3-(2,2-dibromovinyl)-2,2-dimethylcyclopropanecarboxylate.

EXAMPLE III

Preparation of Ethyl 3-(2,2-Dibromovinyl)-2,2-Dimethylcyclopropanecarboxylate Using the Reaction Product of Aluminum and Ethylene Bromide The reaction product of aluminum and ethylene bromide was prepared as follows from 0.405 g (0.015 mole) of aluminum. A catalytic amount of bromine was added as a catalyst to a portion of the aluminum in 5 ml of ethylene bromide. The resultant mixture was heated over an open flame until an exothermic reaction began. The remainder of the aluminum was then added portionwise.

After all of the aluminum dissolved, the mixture was allowed to cool to room temperature, and ethyl 3-(2,2-dichlorovinyl)-2,2-dimethylcyclopropanecarboxylate (2.37 g, 0.01 mole) dissolved in 10 ml of ethylene bromide was added at about 0°. The reaction mixture was allowed to warm to 20°. After 8.5 hours the reaction mixture was poured into ice water, and the resultant mixture was extracted with ether. The ether extract was washed successively with water, aqueous sodium bicarbonate, aqueous sodium chloride, and then it was dried. After removing the ether, the residue was distilled under reduced pressure to afford ethyl 3-(2,2-dibromovinyl)-2,2-dimethylcyclopropanecarboxylate (2.80 g, 94% yield of product 90% pure); bp, 101°–107°/0.27 mm.

EXAMPLE IV

Preparation of Cis-3-(2,2-Dibromovinyl)-2,2-Dimethylcyclopropanecarboxylic Acid Using Aluminum and HBr Anhydrous hydrogen bromide gas was introduced through a pipet (below the liquid level in the flask) to a stirred suspension of a small portion of aluminum shot in methylene bromide (250 ml) at 60°. The temperature was maintained at 60°–65° by heating or cooling as required during the portionwise addition of the aluminum shot (9.67 g, 0.358 mole total). The flow of HBr was maintained until all the aluminum had reacted to produce a cloudy brown mixture. The temperature of the reaction mixture was then reduced to 0°–5°, and a solution of cis-3-(2,2-dichlorovinyl)2,2-dimethylcyclopropanecarboxylic acid (50.0 g, 0.24 mole) in methylene bromide was added dropwise over a period of an hour to the vigorously stirred mixture under a nitrogen atmosphere. The reaction mixture was allowed to stir for 1 hour 20 minutes at 0.5°; then a flow of nitrogen was passed through the reaction mixture at reduced pressure (20 mm) for 1¼ hours. The entire reaction mixture was then poured slowly into a mixture of ice and 1 N hydrochloric acid and extracted twice with diethyl ether. The combined ethereal solution was dried over anhydrous magnesium sulfate, and the ether was removed under reduced pressure, affording a gray-brown solid, which was dried in a vacuum oven, affording 3-(2,2-dibromovinyl)-2,2-dimethylcyclopropanecarboxylic acid (70.7 g). The crude product was recrystallized from hexane and sublimed. The cis-3-(2,2-dibromovinyl)-2,2-dimethylcyclopropanecarboxylic acid thus obtained was 93% pure by glc analysis.

EXAMPLE V

Preparation of 3-(2,2-Dibromovinyl)-2,2-Dimethylcyclopropanecarboxylic Acid Using Aluminum Chloride and HBr Hydrogen bromide gas was introduced through a gas inlet tube into a suspension of aluminum chloride (0.99 g, 7.5 mmole) in methylene bromide (6 ml) at 30°. A solution of 3-(2,2-dichlorovinyl)-2,2-dimethylcyclopropanecarboxylic acid (1.196 g, 5.05 mmole) in methylene bromide was added dropwise, the temperature being controlled with ice-water cooling. The introduction of HBr was reinitiated and continued until all the suspended solid was dissolved and the color of the reaction mixture changed to reddish black. The pressure inside the reaction flask was then reduced to 20 mm while argon gas was bubbled in through a syringe needle. After 3.5 hours the product was isolated as described in Example IV. The yield of 3-(2,2-dibromovinyl)-2,2-dimethylcyclopropanecarboxylic acid was 91.7%.

Following the procedures of Examples I–V the other esters of 3-(2,2-dichlorovinyl)-2,2-dimethylcyclopropanecarboxylic acid and the free acid are converted to the corresponding dibromovinyl compounds.

We claim:

1. A process for preparing 3-(2,2-dibromovinyl)-2,2-dimethylcyclopropanecarboxylic acid or a lower alkyl ester thereof which comprises exchanging the chlorine atoms in 3-(2,2-dichlorovinyl)-2,2-dimethylcyclopropanecarboxylic acid or a lower alkyl ester thereof with bromine atoms wherein said exchange is effected in a solvent with HBr and the product of the reaction of HBr with aluminum or an aluminum salt.

2. The process of claim 1 wherein the solvent is selected from methylene bromide, ethylene bromide, ethyl bromide, carbon disulfide, methylene chloride, and cyclohexane.

3. The process of claim 2 wherein the solvent is methylene bromide.

4. The process of claim 1 conducted at a temperature between about 0° and the boiling point of the solvent.

5. The process of claim 1 conducted under an inert atmosphere.

6. The process of claim 1 wherein 3-(2,2-dibromovinyl)-2,2-dimethylcyclopropanecarboxylic acid is prepared from 3-(2,2-dichlorovinyl)-2,2-dimethylcyclopropanecarboxylic acid.

* * * * *